US006277416B1

(12) United States Patent
Harkrader et al.

(10) Patent No.: US 6,277,416 B1
(45) Date of Patent: Aug. 21, 2001

(54) PESTICIDES COMPRISING BENZOPHENANTHRIDINE ALKALOIDS

(75) Inventors: Ronald J. Harkrader, Westminster; Donald L. Meyer, Fort Collins, both of CO (US)

(73) Assignee: Camas Technologies, Inc., Broomfield, CO (US)

( * ) Notice: Subject to any disclaimer, the term of this patent is extended or adjusted under 35 U.S.C. 154(b) by 0 days.

(21) Appl. No.: 09/662,381

(22) Filed: Jul. 29, 1999

Related U.S. Application Data

(63) Continuation of application No. 08/642,464, filed on May 3, 1996.

(51) Int. Cl.[7] ............................. A01N 65/00; A01N 43/42
(52) U.S. Cl. ........................ 424/725; 514/284; 514/749; 47/58.1
(58) Field of Search ................................ 424/195.1, 725, 424/749; 514/284; 47/58.1; 504/124, 130, 245

(56) References Cited

U.S. PATENT DOCUMENTS

| 3,931,149 | * | 1/1976 | Szkrybola | 536/17.1 |
| 4,406,881 | * | 9/1983 | Ladanyi | 424/49 |
| 5,175,000 | * | 12/1992 | Godowski et al. | 424/426 |
| 5,425,948 | * | 6/1995 | Olivieri | 424/401 |

OTHER PUBLICATIONS

Greathouse et al.; The chemistry of resistance of plants . . . ; Phytopath.; 30; pp. 475–485, 1940.*

* cited by examiner

*Primary Examiner*—Mary E. Mosher
(74) *Attorney, Agent, or Firm*—Steven C. Petersen; Hogan & Hartson, LLP

(57) ABSTRACT

The present invention relates to a chemical composition useful in the chemical management of plant disease. The pesticides of the present invention incorporate benzophenanthridine alkaloids into formulations that are (1) residual and active for a period of time, (2) are adhesive to plant surfaces, (3) have good spreading properties, (4) are stable against photodeactivation, (5) have low phytoxicity, and (6) are capable of penetrating plant tissues.

15 Claims, No Drawings

PESTICIDES COMPRISING BENZOPHENANTHRIDINE ALKALOIDS

CROSS-REFERENCE TO OTHER APPLICATIONS

This patent application is a continuation of U.S. patent application Ser. No. 08/642,464, filed May 3, 1996 and entitled Pesticides Comprising Benzophenanthridine Alkaloids.

BACKGROUND OF THE INVENTION

1. Field of the Invention

The present invention relates to a nonselective chemical composition useful in the chemical management of plant diseases. More specifically, the chemical composition of the present invention incorporates a class of naturally occurring alkaloids having antimicrobial properties.

2. Description of the State of the Art

A plant disease may be defined as any disturbance that prevents the normal development of a plant and reduces its economic or aesthetic value. Infectious plant diseases are caused by living agents (microorganisms), or pathogens, such as, nematodes, fungi, bacteria, mycoplasmas, viruses and viroids, which interfere with the normal function of some part of the plant, resulting in lower yields or reduced quality. Although there are at least 50,000 diseases of economic plants, and new diseases are discovered every year, it is difficult to accurately assess losses from disease. However, it is safe to say that annual losses in the United States average about 15% of the total agricultural production, or more than about $15 billion. Disease causes another $150 million in economic loss in terms of the replacement value and increased maintenance costs of ornamentals and turf in the United States. For the farmer, this leads to less income; for the consumer, reduced food supplies of lower quality and higher prices; and for the homeowner and turf manager, lower aesthetic value, less beauty and higher maintenance costs.

The idea of using chemicals to protect plants from microorganisms or "pests" goes back at least 2000 years. Homer, the Greek poet and author of The Illiad and The Odyssey, wrote about the "pest averting sulfur with its property of divine and purifying fumigation." Broadly speaking, chemicals that are used to kill or inhibit the development of microorganisms are referred to as pesticides. As biological knowledge grew in the eighteenth and nineteenth centuries and as pest problems became more severe as a result of more complex agriculture and the introduction of pests into new areas, the search for effective pest management methods intensified. The discovery in 1882 that spraying grapes with a Bordeaux mixture would reduce damage from downy mildew encouraged scientists to look for other chemicals that would kill pests. Certain chemicals are useful as pesticides because they are more toxic to plant pathogens than they are to plants. Some pesticides are nonselective, that is, toxic to many pathogens; and others are selective, affecting only a few or one kind of pathogen.

In the twentieth century plant pathology matured as a science with startling and rapid discoveries. Since the 1930s, many hundreds of compounds have been screened for chemotherapeutic activity. In most studies, made with the aim of discovering compounds of practical use in the field, activity was measured directly by application to the growing plant; however, this proved to be a slow and laborious screening process. In response, scientists developed more rapid and economic techniques, such as, floating inoculated leaf discs on solutions of the test compounds or using excised petioles, for detecting the movement of antimicrobial chemicals within the plant body.

To date the vast majority of compounds utilized as pesticides have been synthetic organic and inorganic compounds. Because of the growing concerns regarding pesticide damage to the environment scientists have shifted their focus to examining constituents from higher plants for chemotherapeutic activity. Many of these constituents have been implicated in the natural resistance which is shown by plants towards most pathogens. Greathouse, G. A., demonstrated in vitro that quartenary benzophenanthridine alkaloids, the sources of which include five plant families: Papaveraceae, Fumariaceae, Rutaceae, Capifoliaceace, and Meliaceae, influenced the growth of several fingal species, and root rots known as *Phytomatoryrichum omnivorum*. See, Greathouse, G. A., et al., "The Chemistry of Resistance of Plants to Phymatotrichium Root Rot v. Influence of Alkaloids on Growth of Fungi," *Phytopathology* 30:475–485 (1940); and Greathouse, G. A., "Alkaloids from *Sanguinaria canadensis* and Their Influence on Growth of *Phymatotrichium omnivorum*," *Plant Physiology*, 14:377–380 (1939), respectively. In addition to these in vitro studies, plant extracts containing benzophenanthridine alkaloids have been utilized in a number of pharmaceutical compositions for human medical and veterinary treatment applications including ringworm, dysentery, expectorants, scours, antiplaque and anti-gingivitis in oral health care, and anti-inflammation.

The benzophenanthridine alkaloids have been shown to be active in vitro against several fungal and bacterial strains. The minimum concentrations of benzophenanthridine alkaloids inducing complete inhibition of visible growth on Mueller-Hinton media are given in Table 1 for a variety of pathogens.

TABLE 1

IN VITRO ANTIMICROBIAL ACTIVITY
OF BENZOPHENANTHRIDINE ALKALOIDS

| ORGANISM | MINIMUM ANTIMICROBIAL CONCENTRATION OF BENZOPHENANTHRIDINE ALKALOID ug/ml |
|---|---|
| Actinomycetes | 6.25–25 |
| Penicillium | 50–100 |
| Aspergillus | 25–100 |
| Botrytis cinera | 5–50 |
| Rhizoctonia solani | 5–25 |
| Verticillium dahliae | 15–50 |
| Fusarium | 5–25 |
| Erwinia | 20–40 |
| Alternaria | 20–50 |
| Dendryphion | 20–50 |
| Plasmopara | 6.25–25 |
| Phytomatotrichum omnivorum | 2.5–10 |
| Pseudomonas | 175–512 |
| Klebsiella | 17–175 |
| Bacillus | 2–12 |
| Sclerotium | 16–32 |
| Verticillium albo-atrum | 16–32 |
| Fusarium vasinfectrum | 64–256 |
| Pythium | 40–100 |
| Septoria | 5–25 |
| Sphaerotheca pannosa | 5–25 |
| Phytophthera | 16–32 |

Years following Greathouse's discoveries a technical paper by Spencer, et al., was published demonstrating that the compound wyerone, isolated from broad bean tissue also had in vitro antifungal activity. See, Spencer, D. M., et al., "An Antifungal Substance from the Tissue of *Vicia faba*,"

*Nature*, Lond., 179:651 (1957). Since then, naturally-occurring L-amino acids, other than methionine, which have shown little activity and D-isomers which have usually proved more effective have also been studied. Certain analogues of natural amino acids show useful activity; some of these, such as, L-threo-β-phenylserine, apparently operate through an effect on the host, while others, such as, canavanine, ethionine and fluorophenylanine, are fungitoxic antimetabolites which exert a direct action against the pathogen.

Unfortunately, the in vitro studies performed by Greathouse et al., Spencer et al., and others have limited use, since there is rarely a high correlation between in vitro microbial toxicity and therapeutic activity. An additional limitation and complication in the identification of compounds that may be used as pesticides is that chemicals are not usually used in their pure forms, but rather are mixed with inert substances to form pesticide formulations. Pesticide formulations must be prepared so the user can apply it in a safe, convenient, and effective manner.

Many factors affect the ability to place the pesticide on the target in the manner and amount for the most effective results, with the least undesirable side effects, and at the lowest possible cost. While the selection and use of equipment is of utmost importance, successful application is impossible without proper consideration to compatibility and to formulations which (1) are residual and active for a period of time, (2) are adhesive to the plant surface, (3) have good spreading properties, (4) are stable against photodeactivation, (5) have a low phytotoxicity, and (6) are capable of penetrating the plant tissues.

There is still a need, therefore, for a safe, convenient, effective, and nonselective chemical composition for the treatment of plant disease wherein the active ingredients are naturally occurring organic compounds.

SUMMARY OF THE INVENTION

Accordingly, it is an object of this invention to provide a nonselective pesticide comprising naturally occurring organic compounds as the active ingredient.

An additional object of this invention is to develop systemic and topical pesticides to eliminate and control fungal and bacterial infections in plants.

A further object of this invention is to provide a pesticide that may be applied to a plant in the manner and amount for the most effective results, with the least undesirable side effects.

A more specific object of this invention is to provide a nonselective pesticide comprising quartenary benzophenanthridine alkaloids as the active ingredient.

Additional objects, advantages, andnovel features of this inventions shall be set forth in part in the description that follows, and in part will become apparent to those skilled in the art upon examination of the following specification or may be learned by the practice of the invention. The objects and advantages of the invention may be realized and attained by means of the instrumentalities, combinations, compositions, and methods particularly pointed out in the appended claims.

To achieve the foregoing and other objects and in accordance with the purpose of the present invention, as embodied and broadly described therein, the composition of this invention comprises from about 0.001% to 10.0% by weight benzophenanthridine alkaloids, a wetting agent, and a penetration agent carried in an organic solvent thereby producing a pesticide formulation.

DETAILED DESCRIPTION OF THE PREFERRED EMBODIMENTS

The present invention relates to a nonselective pesticide composition or formulation which incorporates a class of alkaloids (commonly referred to as benzophenanthridine alkaloids) having a quinoline nucleus with two benzene rings fused at the 3, 4 and 7, 8 positions of the quinoline. The pesticide formulation is a combination of benzophenanthridine alkaloids, dissolved in a suitable agricultural carrier system which is water compatible. In addition to being a solubilizing medium for the benzophenanthridine alkaloids, the carrier may also incorporate further components which assist the benzophenanthridine alkaloids in spreading across the surface and/or penetrating the surface of a leaf or stem. These components are generally referred to as wetting agents and penetration agents, respectively, (both of which are broadly referred to as surfactants), and translocation agents.

Known sources of benzophenanthridine alkaloids include the plant families: Papaveraceae, Fumariaceae, Rutaceae, Capifoliaceace, and Meliaceae. In the Papaveraceae family there are five plant species known to contain significant quantities of benzophenanthridine alkaloids; *Chelidonium majus, Dicranostigma lactucoides, Eschseholtzia californica, Macleaya cordata* and *Macleaya microcarpa*, and *Sanguinaria canadensis*. Crude extracts containing a number of benzophenanthridine alkaloids obtained from natural plant sources may be used in the present invention, or the individual benzophenanthridine alkaloids in the crude extract may be further separated, purified and used. Methods for the extraction, separation and purification of the various benzophenanthridine alkaloids are given in a technical paper by Forche, E., et al., *Planta Med.*, 42:137–149 (1981), the disclosure of which is incorporated herein by reference. Other methods of extraction, separation and purification can be found in *Collect. Czech Chem. Commun.*, 55:2841–2867, (1990) by Dostal J., et al., the disclosure of which is incorporated herein by reference.

The benzophenanthridine alkaloids can be isolated in two forms, the acid or iminium ion form and the free amine or base form. Derivatives, such as synthetically modified benzophenanthridine alkaloids, and synthetically formed benzophenanthridine alkaloids, may also be used in the present invention. Synthetic methods for preparing derivatives of the iminium ion (water soluble) and synthesized substituted base forms (water insoluble) are disclosed by Simanek, V., et al., *Heterocycles*, 6:475–497 (1977), and in "*Isoquinoline Alkaloids Research*" by Shamma and Monoid, Plenum Publishers, New York, N.Y. (1978), the disclosures of which are incorporated herein by reference.

As way of illustration only, the pesticide formulations discussed in detail below are prepared using a Macleaya extract and it is not meant to limit the scope of plant materials which may be utilized by the present invention as other plant materials containing benzophenanthridine alkaloids, such as *Sanguinaria canadensis, Chelidonium majus, Dicranostigma lactucoides, Macleaya cordata* and *microcarpa, Eschseholtzia californica* etc., may be utilized. The benzophenanthridine alkaloid extract is produced by mixing or contacting a solvent, such as an alcohol, and preferably ethanol or methanol with a finely cut or ground plant material containing benzophenanthridine alkaloids, such as, *Macleaya cordata*. The mixture is thoroughly stirred with several volumes of the solvent for 24 hours or more, at a temperature between 40–70° C., with 50–60° C. being preferred. Subsequently, the solution is filtered and the solvent evaporated. The residue is dissolved in a suitable organic solvent, such as chloroform, treated with concentrated hydrochloric acid, filtered and then dried. For use, the extract containing benzophenanthridine alkaloids or pure individual compounds is dissolved into an aqueous solution such as $C_1$–$C_6$ alcohols or other organic solvents at 40° C.±5° C. Upon dissolution, the mixture is cooled and then the remaining ingredients, such as, wetting agents, that is, wetting agents and/or penetrating agents, translocating agents and preservatives are added.

The preparations generally contain 0.001% by weight and up to 10% by weight of the benzophenanthridine alkaloids, with sanguinarine and chelerythrine as the major benzophenanthridine alkaloid components when Macleaya is used. While anionic surfactants such as sodium lauryl sulfate are often mixed with active fungicidal agents for applications to plants the benzophenanthridine alkaloids are not compatible with these agents. Surfactants which may be mixed with the benzophenanthridine alkaloids include non-ionic wetting agents such as polysorbates, free fatty acids, aliphatic oxylated alcohol, tweens, carboxymethyl cellulose, glycols, alkylarylpolyoxyethylene ethers (X-77® a registered mark of Loveland Industries, Inc., Greeley, Colo.), alkyl polyoxyethylene ethers, polyethylene glycol p-isooctyl-phenyl ether (Triton X-100), aliphatic oxylated alcohols, ethoxylated soybean oils, hydrogenated castor oils, vegetable oils, methylated seed oils, and penetrating agents such as pyrroles, N-alkylpyrrolidone ranging from $C_1$ to $C_{12}$ in alkyl chain length, pyrrolidones, methylated pyrrolidones, and polyvinyl pyrrolidones. These surfactants may be used either alone or mixed. The benzophenanthridine alkaloids have also been found to be compatible with some cationic agents such as the betaines, amido betaines, and pyrrolidones in combination with a nonionic surfactant.

Formulations:

An example of a basic formulation:

| Raw Materials | By Weight |
| --- | --- |
| (1) Methanol | 56.25% |
| (2) X-77 ® | 3.13% |
| (3) Macleaya Extract | 0.38% |
| (4) Water | 40.24% |

Dilution Ratio 1:20

A second example of a formulation:

| Raw Materials | By Weight |
| --- | --- |
| (1) Methanol | 78.75% |
| (2) Polyvinyl pyrrolidone | 2.19% |
| (3) Polysorbate 80 | 2.19% |
| (4) Macleaya Extract | 0.53% |
| (5) Methyl pyrrole | 8.75% |
| (6) Water | 7.59% |

Dilution Ratio 1:35

A third example of a formulation:

| Raw Materials | By Weight |
| --- | --- |
| (1) Methanol | 78.75% |
| (2) 1-Methyl Pyrrolidone | 8.75% |
| (3) X-77 ® | 4.38% |
| (4) Macleaya Extract | 0.53% |
| (5) Water | 7.59% |

Dilution Ratio 1:35

A fourth example of a formulation:

| Raw Materials | By Weight |
| --- | --- |
| (1) Methanol | 56.25% |
| (2) Macleaya Extract | 0.38% |
| (3) 1-Methyl Pyrrolidone | 6.25% |
| (4) X-77 ® | 3.13% |
| (5) Water | 33.99% |

Dilution Ratio 1:85

A fifth example of a formulation:

| Raw Materials | By Weight |
| --- | --- |
| (1) Acetone | 5.00% |
| (2) X-77 ® | 0.50% |
| (3) Triton x-100 | 1.00% |
| (3) Macleaya Extract Base Form | 0.06% |
| (4) 20% Sodium Hydroxide | 0.01% |
| (5) Water | 94.43% |

Dilution Ratio 1:8

A sixth example of a formulation:

| Raw Materials | By Weight |
| --- | --- |
| (1) Ethanol | 82.50% |
| (2) Hydrogenated Caster Oil | 6.00% |
| (3) Triton X-100 | 1.00% |
| (4) n-Octyl Pyrrolidone | 1.00% |
| (5) Macleaya Extract | 1.00% |
| (6) Water | 8.50% |

Dilution Ratio 1:30

A seventh example of a formulation:

| Raw Materials | By Weight |
| --- | --- |
| (1) Methanol | 5.00% |
| (2) Macleaya Extract | 0.06% |
| (3) Polyvinyl Pyrrolidone | 0.25% |
| (4) X-77 ® | 0.25% |
| (5) Water | 94.44% |

Dilution Ratio 1:4

An eighth example of a formulation:

This formulation is prepared by mixing Macleaya Extract with water to form a fluid extract of 1.5% by weight.

| Raw Materials | By Weight |
| --- | --- |
| (1) Butanol | 15.00% |
| (2) Macleaya Extract Fluid Extract (1.5%) | 0.04% |
| (3) Carboxymethyl Cellulose | 0.50% |
| (4) 1-methyl pyrrolidone | 1.00% |
| (5) Water | 83.46% |

Dilution Ratio 1:8

A ninth example of a formulation:

| Raw Materials | By Weight |
| --- | --- |
| (1) Alkyl polyethoxy ether | 0.25% |
| (2) Soy wet surfactant | 0.10% |
| (3) Macleaya Extract | 0.15% |
| (4) Polyethylene glycol 200 | 0.50% |
| (5) Polyvinyl pyrrolidone 30 | 0.25% |
| (6) Methanol | 5.00% |
| (7) Water | 93.75% |

Dilution Ratio 1:6 when used for foliar and drench applications.
Dilution Ratio 1:30 when used for tuber treatment.

A tenth example of a formulation:

| Raw Materials | By Weight |
| --- | --- |
| (1) Acetone | 4.00% |
| (2) 2-Pyrrolidone | 1.00% |
| (3) Macleaya Extract Base Form | 0.05% |
| (4) Vegetable Oil Surfactant | 0.25% |
| (5) Triton X-100 | 0.25% |
| (6) Water | 94.44% |
| (7) 25% Sodium Hydroxide | 0.01% | ph 7.5
Dilution Ratio 1:4 or 1:8

An eleventh example of a formulation:

| Raw Materials | By Weight |
| --- | --- |
| (1) Methanol | 74.24% |
| (2) N-Methyl Pyrrolidone | 5.91% |
| (3) X-77 ® | 4.00% |
| (4) Macleaya Extract | 0.56% |
| (5) Water | 15.29% |

Dilution Ratio 1:32

A twelveth example of a formulation:

| Raw Materials | By Weight |
| --- | --- |
| (1) N-Methyl Pyrrolidone | 5.0% |
| (2) Macleaya Extract Base Form | 0.5% |
| (3) HCO-5 (Hydro Castor Oil) | 0.5% |
| (4) Water pH 7.2 | 94.0% |

Dilution Ratio 1:4 or 1:8

A thirteenth example of a formulation:

| Raw Materials | By Weight |
| --- | --- |
| (1) Methanol | 73.60% |
| (2) N-Methyl pyrrolidone | 5.80% |
| (3) Vinyl Pyrrolidone 30 | 2.40% |
| (4) Macleaya Extract Base Form | 0.06% |
| (5) Water | 15.10% |
| (6) Sodium Hydroxide (1 Molar) | 0.10% |

Dilution Ratio 1:70

A fourteenth example of a formulation:

| Raw Materials | By Weight |
| --- | --- |
| (1) N-Methyl Pyrrolidone | 6.16% |
| (2) Methanol | 88.30% |
| (3) X-77 ® | 4.50% |
| (4) Macleaya Extract Base Form | 0.51% |

Dilution Ratio 1:32

A fifteenth example of a formulation:

| Raw Materials | By Weight |
| --- | --- |
| (1) Methanol | 76.80% |
| (2) N-Methyl Pyrrolidone | 3.20% |
| (3) X-77 ® | 4.00% |
| (4) Macleaya Extract | 0.56% |
| (5) Water | 15.44% |

Dilution Ratio 1:32

A sixteenth example of a formulation:

| Raw Materials | By Weight |
| --- | --- |
| (1) Methanol | 80.00% |
| (2) N-Methyl Pyrrolidone | 0.00% |
| (3) X-77 ® | 4.00% |
| (4) Macleaya Extract | 0.56% |
| (5) Water | 15.44% |

Dilution Ratio 1:32

A seventeenth example of a formulation:

| Raw Materials | By Weight |
| --- | --- |
| (1) Methanol | 73.60% |
| (2) N-Methyl Pyrrolidone | 6.40% |
| (3) X-77 ® | 4.00% |
| (4) Macleaya Extract | 0.56% |
| (5) Water | 15.44% |

Dilution Ratio 1:35

A eighteenth example of a formulation:

| Raw Materials | By Weight |
| --- | --- |
| (1) Methanol | 75.23% |
| (2) N-Methyl Pyrrolidone | 18.00% |
| (3) 8-Octyl Pyrrolidone | 2.50% |
| (4) Polyvinyl Pyrrolidone | 2.50% |
| (4) Macleaya Extract | 1.77% |
| (5) Water | 0.00% |

Dilution Ratio 1:100

EXAMPLE I

Phytotoxicity Evaluations of Benzophenanthridine Alkaloid Formulations

A. Phytotoxicity on Roses.

Hybrid Tea roses grown for cut flowers were evaluated for phytotoxic responses to spray applications of the present invention at 25, 50, 75, 100, 150 and 300 ppm benzophenanthridine alkaloids. Placebo formulations comprising carriers and surfactants without benzophenanthridine alkaloids were included at similar rates. Stem length was measured one week after spray application as a measure of phytotoxicity. Table 2, below, summarizes the phytotoxicity results of four formulations of the present invention. Few differences were detected between formulation rates and the data were subsequently pooled. None of the formulations of the present invention or their respective placebo formulations appeared to be phytotoxic to the roses at the rates tested.

TABLE 2

STEM GROWTH OF ROSES ONE WEEK FOLLOWING APPLICATION OF THE PESTICIDE FORMULATIONS OF THE PRESENT INVENTION

| Rate (ppm) | Stem Growth (cm) | | | | | | |
|---|---|---|---|---|---|---|---|
| | Formulation 1st | Placebo | Formulation 4th | Placebo | Formulation 5th | Placebo | Formulation 8th | Placebo |
| 600 | 5.75 | 5.33 | 10.00 | 12.83 | 1.42 | 3.75 | 6.42 | 3.50 |

B. Phytotoxicity on Perennial and Annual Bedding Plants.

Perennial and annual bedding plants grown in 10 cm azalea pots containing peat-lite medium were evaluated for phytotoxic response to a 20% (100 ppm benzophenanthridine alkaloids) root-zone drench application of the present invention. Placebo formulations comprising carriers and surfactants without benzophenanthridine alkaloids were included at similar rates. The plants were examined one week after application of the formulations of the present invention. Table 3, below, summarizes the phytotoxicity rating for 12 perennial plant species subjected to 100 ml of 100 ppm of various formulations of the present invention. Phytotoxicity was observed as folar necrosis and plant death. In all cases where the formulation showed phytotoxicity, the placebo formulations demonstrated similar phytotoxic responses and consequently the data were pooled. The phytotoxicity was related to the carriers and surfactants and not the benzophenanthridine alkaloids. The results from the annual bedding plant experiment were similar.

TABLE 3

Formulations of the Present Invention
(placebo and product pooled)
Phytotoxicity Ratings
(1 = no damage and 5 = dead plant)

| Perennial Species | 1st | 4th | 5th | 7th | 8th | 12th |
|---|---|---|---|---|---|---|
| *Ajuga reptans* | 1.00 | 3.00 | 1.00 | 1.00 | 1.00 | 2.33 |
| *Aquilegia canadenis* | 1.00 | 3.17 | 1.00 | 1.00 | 1.00 | 3.17 |
| *Arabis alpina* | 1.00 | 2.17 | 1.00 | 1.00 | 1.00 | 2.33 |
| *Campanula glomerata* | 1.00 | 2.50 | 1.00 | 1.00 | 1.00 | 2.33 |
| *Delospemia nubigenum* | 1.00 | 1.00 | 1.00 | 1.00 | 1.00 | 1.00 |
| *Erysium kotscliyanum* | 1.00 | 2.00 | 1.00 | 1.00 | 1.00 | 2.50 |
| *Iberis sempervirens* | 1.00 | 1.83 | 1.00 | 1.00 | 1.00 | 1.50 |
| *Lamium maculatum* | 1.00 | 3.50 | 1.00 | 1.00 | 1.00 | 3.17 |
| *Limonium latifolia* | 1.00 | 1.00 | 1.00 | 1.00 | 1.00 | 1.00 |
| *Phlox subulata* | 1.17 | 2.17 | 1.00 | 1.00 | 1.00 | 2.17 |
| *Sagina subulata* | 1.00 | 2.00 | 1.00 | 1.00 | 1.00 | 2.17 |
| *Sedum acre* | 1.00 | 1.00 | 1.00 | 1.00 | 1.00 | 1.00 |
| Mean | 1.00 | 2.11 | 1.00 | 1.00 | 1.00 | 2.06 |

EXAMPLE II

Effect of Benzophenanthridine Alkaloid Formulations of the Present Invention on Plant Pathogens A. Rose.

Powdery Mildew (*Sphaerotheca pannosa*). Rose powdery mildew is one of the most important and troublesome diseases of cultivated roses. The in vivo activity of three formulations of the present invention and their respective placebos were evaluated against rose powdery mildew in a greenhouse environment. Rose powdery mildew was induced on the rose plants prior to applying formulations of the present invention. At the time of application, fungal coverage of the rose leaves was 50.4%. Test formulas were applied at 75, 150 and 300 mg/liter (ppm) as foliar sprays to the rose foliage during two applications at 7 day intervals. Scoring of the rose powdery mildew remaining on the rose leaves was conducted on the third, fifth and tenth days of the trial. The percent leaflet covered by powdery mildew spores and mycelium was evaluated and recorded. The effects of the benzophenanthridine alkaloid formulations of the present invention on rose powdery mildew are sumnarized below in Table 4.

TABLE 4

| Rate (ppm) | Test Day | % fungal coverage on leaf | | |
|---|---|---|---|---|
| | | 1st Formulation | 7th Formulation | 8th Formulation |
| 0 | 3 | 23.3 | 40.4 | 11.2 |
| | 5 | 17.9 | 22.9 | 12.9 |
| | 10 | 11.2 | 22.9 | 6.2 |
| 75 | 3 | 7.5 | 13.8 | 28.8 |
| | 5 | 6.2 | 8.8 | 13.8 |
| | 10 | 1.2 | 0.0 | 5.0 |
| 150 | 3 | 47.5 | 22.5 | 13.8 |
| | 5 | 13.8 | 2.5 | 25.0 |
| | 10 | 17.5 | 6.2 | 5.0 |
| 300 | 3 | 13.8 | 11.2 | 7.5 |
| | 5 | 12.5 | 2.5 | 15.0 |
| | 10 | 5.0 | 6.2 | 1.2 |

Subsequent studies, summarized in Table 5, for powdery mildew control on greenhouse roses were conducted wherein copper sulfate pentahydrate (Phyton-27 5.5 EC), piperlin (Pipron 82.4 EC), and fenarimol (Rubigan 12.5 EC) were included for comparison against a benzophenanthridine alkaloid formulation of the present invention. Spray applications were conducted on day zero and day nine. All commercial fungicides were applied at their respective label rates and the benzophenanthridine alkaloid formulation was applied at 150 ppm benzophenanthridine alkaloid.

TABLE 5

| Days After Application | % fungal coverage on leaf | | | |
|---|---|---|---|---|
| | 11th Formulation | $CuSO_4.5H_2O$ | Piperalin | Fenarimol |
| 0 | 30.0 | 28.3 | 30.0 | 28.3 |
| 1 | 13.5 | 7.1 | 4.3 | 12.1 |
| 4 | 10.0 | 6.4 | 4.3 | 10.7 |
| 7 | 5.3 | 6.6 | 6.0 | 10.0 |
| 9 | 3.9 | 6.3 | 7.5 | 9.0 |
| 11 | 3.9 | 5.7 | 4.5 | 8.3 |

These results indicate that the eleventh benzophenanthridine alkaloid formulation of the present invention is effective in controlling powdery mildew on greenhouse roses within seven days to a level equal to or better than the three commercial fungicides tested.

Formulation 13 (data not shown) was also effective against rose powdery mildew. The mildew was eradicated and controlled in 3 to 5 days.

B. Cucumber seedling.

Stem rot (*Rhizoctonia solani*). The in vivo activity of five formulations of the present invention and their respective placebo were evaluated against *Rhizoctonia solani*. Three to five grams of *Rhizoctonia solani* inoculum was blended into a commercial sphagnum peat moss-based root-zone containing no pine bark in 10 cm plastic pots. The pots containing the inoculum were moistened with water and allowed to incubate for 24 hours. After the 24 hour incubation period, cucumber seedlings were transplanted into each pot and maintained under intermittent mist in a greenhouse. Test formulas were applied at 75, 150 and 300 ppm as a drench (100 ml/pot) to the seedlings. Five of the pots were treated immediately after transplant and five were treated five days after transplant. Treated plants were evaluated for death and wilting indicating Rhizoctonia solani infection. Roots of infected plants were evaluated to confirm Rhizoctonia solani infection. Table 6 summarizes the effect of the benzophenanthridine alkaloid formulations of the present invention on control of soil-borne Rhizoctonia solani infection on cucumber seedlings.

TABLE 6

Seedlings lost per pot (five maximum)

| Rate (ppm) | Formulation 1st | Placebo | Formulation 3rd | Placebo | Formulation 4th | Placebo | Formulation 5th | Placebo | Formulation 7th | Placebo |
|---|---|---|---|---|---|---|---|---|---|---|
| 75 | 0.33 | 1.67 | 0.67 | 0.61 | 0.00 | 0.67 | 1.00 | 1.67 | 0.67 | 2.00 |
| 150 | 0.33 | 1.00 | 1.00 | 0.67 | 3.67 | 2.67 | 1.67 | 0.67 | 0.67 | 3.33 |
| 300 | 0.67 | 0.67 | 0.00 | 0.00 | 5.00 | 5.00 | 2.67 | 1.67 | 1.67 | 3.67 |
| Mean | 0.44 | 1.11 | 0.56 | 0.44 | 2.89 | 2.78 | 1.78 | 0.78 | 1.00 | 3.00 |

Disease control was noted for the first and seventh formulations when comparing the number of seedlings lost with formulations containing benzophenanthridine alkaloid to the placebo formulations. The fifih and fourth formulations exhibited a great deal of phytotoxicity similar to that observed in earlier studies with perennial bedding plants.

Formulation 14 (data not shown) was effective as a drench against stem rot on cucumbers at 20mg/L.

C. Grapes.

Downy mildew (Plasmopara). The in vivo activity of the first preparation of the present invention was evaluated for the control of grape downy mildew in a greenhouse environment. Grape downy mildew was induced on the grape plants prior to applying a formulation of the present invention. At the time of application fungal coverage of the grape leaves was 85%. The test formula was applied at 400, 100, 25, 6.25, and 1.56 mg/liter (ppm) as a foliar spray to the grape foliage. Scoring of the grape downy mildew remaining on the leaves was conducted on the first and fourth days of the trial. The percent leaflet covered by grape downy mildew spores and mycelium was evaluated and recorded. The effects of the benzophenanthridine alkaloid formulation on grape downy mildew is summarized below in Table 7.

TABLE 7

| Rate | Percent fungal control | |
|---|---|---|
| (ppm) | 24 hours | 96 hours |
| 400 | 100 | No data |
| 100 | 96 | 94 |
| 25 | 97 | 85 |
| 6.25 | 29 | 0 |
| 1.56 | 29 | 0 |

Formulation 13 (data not shown) was also effective against grape downy mildew. The mildew was eradicated and controlled in 3 to 5 days.

D. Tomato.

Leaf blight (*Phytophtera infestans*). Formulation eleven was shown to control 100% of tomato leaf blight at 75 mg/L.

E. Potato.

Brown rot (*Fusarium roseum*). Formulation twelve was shown to be effective in preventing brown rot in the potato.

The foregoing description is considered as illustrative only of the principles of the invention. Furthermore, since numerous modifications and changes will readily occur to those skilled in the art, it is not desired to limit the invention to the exact construction and process shown as described above. Accordingly, all suitable modifications and equivalents may be resorted to falling within the scope of the invention as defined by the claims which follow.

What is claimed is:

1. A method for the treatment of a plant having a systemic disease, comprising:

applying to the diseased plant a therapeutic quantity of solution comprising about 0.001% to 10.00% by weight of benzophenanthridine alkaloids in a carrier system having at least one wetting agent and having at least one penetration agent, wherein said solution is absorbed into the diseased plant.

2. The method of claim 1, wherein said systemic disease is caused by a bacterium.

3. The method of claim 1, wherein said systemic disease is caused by a powdery mildew.

4. The method of claim 1, wherein said systemic disease is caused by a downy mildew.

5. The method of claim 1, wherein said systemic disease is caused by a leaf blight.

6. The method of claim 1, wherein said therapeutic quantity of solution is applied as a drench to the soil surrounding said diseased plant.

7. The method of claim 1, wherein said therapeutic solution is applied as a foliar spray.

8. The method of claim 1, wherein said therapeutic solution has a concentration by weight of said benzophenanthridine alkaloids is about 0.001% to 10.0%.

9. A method for the treatment of a plant having a systemic disease, comprising:

applying to the diseased plant a therapeutic quantity of solution comprising about 0.001% to 10.0% by weight of said benzophenanthridine alkaloids, about 0.1% to 25% by weight 1-Methyl Pyrrolidone, about 0.02% to 15% by weight alkylarylpolyethylene ether, about 0.8% to 80% by weight alcohol, and about 0% to 95% water.

10. The method of claim 9, wherein said systemic disease is caused by a bacterium.

11. The method of claim 9, wherein said systemic disease is caused by a powdery mildew.

12. The method of claim 9, wherein said systemic disease is caused by a downy mildew.

13. The method of claim 9, wherein said systemic disease is caused by a leaf blight.

14. The method of claim 9, wherein said therapeutic quantity of solution is applied as a drench to the soil surrounding said diseased plant.

15. The method of claim 9, wherein said therapeutic solution is applied as a foliar spray.

* * * * *